United States Patent [19]

Abbondi et al.

[11] Patent Number: 5,976,509
[45] Date of Patent: Nov. 2, 1999

[54] COMPOSITION FOR ODONTOSTOMATOLOGICAL USE IN CLEANING AND DISINFECTING THE ROOT CANALS AND VIABLE DENTINE

[76] Inventors: Thomas Abbondi, Via Torricelli, 10/25 - Genova; Marco Rotondi, Piazza Rotonda, 1 - Genova; Alfredo Capellino, Salita S. Rocco, 22/3 - Genova, all of Italy

[21] Appl. No.: 09/077,349

[22] PCT Filed: Nov. 28, 1996

[86] PCT No.: PCT/IT96/00232

§ 371 Date: May 26, 1998

§ 102(e) Date: May 26, 1998

[87] PCT Pub. No.: WO97/19597

PCT Pub. Date: Jun. 5, 1997

[30] Foreign Application Priority Data

Nov. 29, 1995 [IT] Italy .................................. 6E95A0132

[51] Int. Cl.⁶ .............................. A61K 7/20; A61K 33/20
[52] U.S. Cl. ............................................. 424/53; 424/661
[58] Field of Search ....................................... 424/53, 661

[56] References Cited

U.S. PATENT DOCUMENTS

| 1,435,498 | 11/1922 | Resnik ...................................... 424/53 |
| 3,932,605 | 1/1976 | Vit .............................................. 424/49 |
| 3,998,945 | 12/1976 | Vit .............................................. 424/53 |
| 4,155,975 | 5/1979 | Ricky ............................................ 422/5 |
| 4,755,354 | 7/1988 | Trinh et al. ................................ 422/37 |
| 4,772,414 | 9/1988 | Marzec et al. . |
| 4,780,216 | 10/1988 | Wojtowicz . |
| 4,918,181 | 4/1990 | Karcher et al. .......................... 536/114 |
| 5,049,385 | 9/1991 | Wiedrich et al. ........................ 424/408 |
| 5,106,559 | 4/1992 | Wiedrich et al. ........................ 264/122 |
| 5,281,392 | 1/1994 | Rubenstein ................................ 422/28 |
| 5,599,571 | 2/1997 | Estrada ..................................... 426/321 |
| 5,709,992 | 1/1998 | Rubenstein ................................ 435/2 |
| 5,753,602 | 5/1998 | Hung et al. .............................. 510/192 |
| 5,817,337 | 10/1998 | DeSenna ................................. 424/466 |

FOREIGN PATENT DOCUMENTS

WO 90/00006 1/1990 WIPO .
WO 94/28722 12/1994 WIPO .

Primary Examiner—Shep K. Rose
Attorney, Agent, or Firm—Akin, Gump, Strauss, Hauer & Feld, L.L.P.

[57] ABSTRACT

A liquid composition for use as an odontostomatological aid comprises a water solution of suitable amounts of calcium hypochlorite and potassium chloride. The composition is valuable in therapy owing to its many properties as disinfectant, lubricant, stabilizer, enzyme activator, immunosuppressor, analgesic and haemostatic agent.

2 Claims, No Drawings

COMPOSITION FOR ODONTOSTOMATOLOGICAL USE IN CLEANING AND DISINFECTING THE ROOT CANALS AND VIABLE DENTINE

This application is a 971 of PCT /IT96/00232 filed Nov. 28, 1996 based on Italy 6E95A000 132 filed Nov. 29, 1995.

BACKGROUND OF THE INVENTION

The present invention relates to compositions for therapeutic use, and in particular to an aqueous solution to be used in the odontostomatological field.

It is known that in oral surgery, such as odontotripsy, tooth extraction, apicectomy and so on it is imperative to accurately clean and disinfect the concerned area in order to avoid subsequent complications and/or infections. Such post-surgery operations are usually carried out by using suitable solutions containing for example surfactant agents (e.g. quaternary ammonium compounds), hydrogen peroxide or other oxygen delivering compounds, or especially sodium hypochlorite (NaOCl).

However the above disinfecting solutions are sometimes not devoid of undesirable side effects, or have not at least some desirable properties such as analgesic, osteogenic or cicatrizing activity. Sodium hypochlorite has for instance the following drawbacks: cytotoxic effects on vital tissues, allergy, massive apical extrusion.

SUMMARY OF THE INVENTION

The present inventors have now surprisingly found that a particular combination of $OCl^-$, $Ca^{++}$ and $K^+$ ions does effectively show all of the above desirable properties.

The object of the present invention is therefore to provide an aqueous solution comprising suitable amounts of said ions, which solution is endowed with the following properties:

high disinfecting, lubricating, bleaching action;

disintegrating and dissolving activity against necrotic residues and dentinal debris;

very low toxicity with respect to the oral mucosa and in particular to periapical tissues;

remarkable analgesic activity against post-surgical pain;

remarkable improvement in the osteogenic and cicatrizing process of injured tissues;

stabilizing effect on cell membranes;

haemostatic activity.

DETAILED DESCRIPTION OF THE INVENTION

The solution according to the present invention is obtained by dissolving in distilled water at room temperature an amount of potassium chloride from 0,1% wt/vol to 10% wt/vol, and an amount of calcium hypochlorite to give about 5% wt/vol active chlorine. According to a preferred embodiment the proportion of KCl is 3% wt/vol. A possible ensuing turbidity can be removed by sedimentation or filtration, or as an alternative it may be left in suspension being by no way harmful.

In use, the thus prepared solution may be applied as such or after appropriate dilution according to the mouth conditions, individual sensitivity, patient's age, etc. The application of said multivalent disinfecting solution is usually effected on the root canals by means of a needle-bearing syringe in order to carefully irrigate each single canal.

The particular composition of the present solution thanks to the coexistence of hypochlorous and calcium ions allows said solution, contrary to any other available canalar irrigating liquid, to be used also as an "intermediate canalar medicament".

The present invention has been described with reference to a particular embodiment thereof, i.e. as a disinfecting liquid for oral usage, but it is to be understood that other application forms could be envisaged by those skilled in the art, both regarding the formulation of the solution and the application field. For example it would be possible to use the claimed solution as a simple collutory or as a cleaning and disinfecting aid in other surgical areas.

We claim:

1. A disinfecting solution containing hypochlorite, calcium and potassium ions, characterized in that it comprises an aqueous solution containing from 0.1% wt/vol to 10% wt/vol potassium chloride, and an amount of calcium hypochlorite suitable to yield about 5% wt/vol of active chlorine dissolved in water.

2. The disinfecting solution according to claim 1, characterized in that the concentration of potassium chloride is 3% wt/vol.

* * * * *